United States Patent
Johnson et al.

(10) Patent No.: US 10,018,356 B2
(45) Date of Patent: Jul. 10, 2018

(54) SYSTEM AND METHOD FOR CONTROLLING ONE OR MORE PROCESS PARAMETERS ASSOCIATED WITH A COMBUSTION PROCESS

(71) Applicant: Babcock & Wilcox Power Generation Group, Inc., Barberton, OH (US)

(72) Inventors: Daniel B. Johnson, Orland Park, IL (US); Shannon R. Brown, Doylestown, OH (US)

(73) Assignee: The Babcock & Wilcox Company, Barberton, OH (US)

( * ) Notice: Subject to any disclaimer, the term of this patent is extended or adjusted under 35 U.S.C. 154(b) by 915 days.

(21) Appl. No.: 13/837,221

(22) Filed: Mar. 15, 2013

(65) Prior Publication Data

US 2014/0196639 A1 Jul. 17, 2014
US 2017/0227216 A9 Aug. 10, 2017

Related U.S. Application Data

(63) Continuation-in-part of application No. 13/832,065, filed on Mar. 15, 2013, now Pat. No. 9,457,316.

(60) Provisional application No. 61/752,167, filed on Jan. 14, 2013, provisional application No. 61/671,007, filed on Jul. 12, 2012.

(51) Int. Cl.
| | |
|---|---|
| *F23J 15/02* | (2006.01) |
| *G01N 31/12* | (2006.01) |
| *G01N 33/18* | (2006.01) |
| *G01N 31/00* | (2006.01) |
| *G01N 1/22* | (2006.01) |

(52) U.S. Cl.
CPC .............. *F23J 15/02* (2013.01); *G01N 1/22* (2013.01); *G01N 31/005* (2013.01); *G01N 31/12* (2013.01); *G01N 33/1846* (2013.01)

(58) Field of Classification Search
CPC ...... G01N 31/12; G01N 1/22; G01N 33/1846; G01N 31/005; F23J 15/02
See application file for complete search history.

(56) References Cited

U.S. PATENT DOCUMENTS

| | | | | |
|---|---|---|---|---|
| 2,307,929 A | | 1/1943 | Joyce, Jr. | |
| 3,984,522 A | * | 10/1976 | Saito ....................... | B01D 53/56 423/235 |
| 4,151,263 A | * | 4/1979 | Ciuryla ................ | B01D 53/501 423/243.06 |
| 4,364,752 A | * | 12/1982 | Fitch ......................... | B03C 3/38 361/230 |
| 4,533,440 A | * | 8/1985 | Kim ...................... | B01D 53/346 204/400 |
| 2006/0047366 A1 | * | 3/2006 | Boyden ................ | G05B 13/048 700/266 |
| 2008/0202331 A1 | * | 8/2008 | Abdelkrim ................ | B03C 3/08 95/5 |
| 2008/0233024 A1 | * | 9/2008 | Lindau ................. | B01D 53/346 423/110 |
| 2009/0130013 A1 | * | 5/2009 | Higgins ................. | B01D 53/64 423/242.1 |
| 2010/0061190 A1 | | 3/2010 | Kawamura et al. | |
| 2013/0064748 A1 | * | 3/2013 | Dube ................... | B01D 53/501 423/243.08 |
| 2013/0180923 A1 | * | 7/2013 | Keiser .................... | B01D 53/96 210/662 |

FOREIGN PATENT DOCUMENTS

| | | |
|---|---|---|
| CN | 100496672 C | 6/2009 |
| EP | 1106237 B1 | 10/2004 |
| WO | 2012/176635 A1 | 12/2012 |

* cited by examiner

*Primary Examiner* — Krishnan S Menon
*Assistant Examiner* — Dwan A Gerido
(74) *Attorney, Agent, or Firm* — Michael J. Seymour

(57) ABSTRACT

The present invention relates generally to the generation of steam via the use of a combustion process to produce heat and, in one embodiment, to a device, system and/or method that enables one to control one or more process parameters of a combustion process so as to yield at least one desirable change in at least one downstream parameter. In one embodiment, the present invention is directed to a system and/or method for controlling at least one process parameter of a combustion process so as to yield at least one desirable change in at least one downstream process parameter associated with one or more of a wet flue gas desulfurization (WFGD) unit, a particulate collection device and/or control of additives thereto and/or a nitrogen oxide control device and/or control of additives thereto and/or additives to the system.

23 Claims, No Drawings

SYSTEM AND METHOD FOR CONTROLLING ONE OR MORE PROCESS PARAMETERS ASSOCIATED WITH A COMBUSTION PROCESS

RELATED APPLICATION DATA

This patent application is a continuation-in-part of U.S. patent application Ser. No. 13/832,065 filed Mar. 15, 2013 and titled "Method for Controlling Compounds and Conditions in a Wet Flue Gas Desulfurization (WFGD) Unit, which itself claims priority to and is a non-provisional of U.S. Provisional Patent Application No. 61/671,007 filed Jul. 12, 2012 and titled "Method for Controlling Compounds and Conditions in a Wet Flue Gas Desulfurization (WFGD) Unit." The present application also claims priority to and is a non-provisional of U.S. Provisional Patent Application No. 61/752,167 filed Jan. 14, 2013 and titled "System and Method for Controlling One or More Process Parameters in a Combustion Process." The complete texts of these applications are hereby incorporated by reference as though fully set forth herein in their entireties.

FIELD AND BACKGROUND OF THE INVENTION

1. Field of the Invention

The present invention relates generally to the generation of steam via the use of a combustion process to produce heat and, in one embodiment, to a device, system and/or method that enables one to control one or more process parameters of a combustion process so as to yield at least one desirable change in at least one downstream parameter. In one embodiment, the present invention is directed to a system and/or method for controlling at least one process parameter of a combustion process so as to yield at least one desirable change in at least one downstream process parameter associated with one or more of a wet flue gas desulfurization (WFGD) unit, a particulate collection device and/or control of additives thereto and/or a nitrogen oxide control device and/or control of additives thereto and/or additives to the system. In another embodiment, the present invention is directed to a system and/or method for controlling at least two process parameters of a combustion process so as to yield at least one desirable change in at least one downstream process parameter associated with one or more of a wet flue gas desulfurization (WFGD) unit, a particulate collection device and/or control of additives thereto and/or a nitrogen oxide control device and/or control of additives thereto and/or additives to the system.

2. Description of the Related Art

A variety of $SO_2$ control processes and technologies are in use and others are in various stages of development. Commercialized processes include wet, semidry (slurry spray with drying) and completely dry processes. The wet flue gas desulfurization (WFGD) scrubber is the dominant worldwide technology for the control of $SO_2$ from utility power plants, with approximately 85 percent of the installed capacity, although the dry flue gas desulfurization (DFGD) systems are also used for selected lower sulfur applications.

Wet scrubbing processes are often categorized by reagent and other process parameters. The primary reagent used in wet scrubbers is limestone. However, any alkaline reagent can be used, especially where site-specific economics provide an advantage. Other common reagents are lime (CaO), magnesium enhanced lime (MgO and CaO), ammonia ($NH_3$), and sodium carbonate ($Na_2CO_3$).

A number of the wet processes are also classified as either non-regenerable or regenerable systems. In non-regenerable systems, the reagent in the scrubber is consumed to directly generate a byproduct containing the sulfur, such as gypsum. In regenerable systems, the spent reagent is regenerated in a separate step to renew the reagent material for further use and to produce a separate byproduct, such as elemental sulfur. The dominant limestone and lime reagent systems used today are non-regenerable. In many cases the regenerable systems have been retrofitted with non-regenerable limestone or lime reagent systems to reduce costs and improve unit availability.

As known to those of skill in the art, the most common WFGD absorber module is the spray tower design (see, e.g., *Steam/its generation and use*, 41st Edition, Kitto and Stultz, Eds., Copyright 2005, The Babcock & Wilcox Company, Barberton, Ohio, U.S.A., particularly Chapter 35—Sulfur Dioxide Control, the text of which is hereby incorporated by reference as though fully set forth herein). In the most common WFGD set-up the flue gas enters the side of the spray tower at approximately its midpoint and exits through a transition at the top. The upper portion of the module (absorption zone) provides for the scrubbing of the flue gas to remove the $SO_2$ while the lower portion of the module serves as an integral slurry reaction tank (also frequently referred to as the recirculation tank (or absorber recirculation tank) and oxidation zone) to complete the chemical reactions to produce gypsum. The self-supporting absorber towers typically range in diameter from 20 feet to 80 feet (6 meters to 24 meters) and can reach 150 feet (46 meters) in height. In some designs, the lower reaction tank is flared downward to provide a larger diameter tank for larger slurry inventory and longer retention time. Other key components include the slurry recirculation pumps, interspatial spray headers and nozzles for slurry injection, moisture separators to minimize moisture carryover, oxidizing air injection system, slurry reaction tank agitators to prevent settling, and the perforated tray to enhance $SO_2$ removal performance.

It has been found that higher concentrations (generally above about 700 ppm) of one or more oxidizers including, but not limited to persulfate, permanganate, manganate, ozone, hypochlorite, chlorate, nitric acid, iodine, bromine, chlorine, fluorine, or combinations of any two or more thereof, coupled with thermodynamically favorable pH and oxidation-reduction potential (ORP) (generally above 500 mV) conditions in the wet scrubber, will cause soluble manganese ($Mn^{2+}$) to form $Mn_xO_y$ precipitate, as well as impact upon the nature, the amount and/or the conditions of mercury reemission and selenium emission from the WFGD. Additionally, the ORP in a WFGD can impact emission rate and/or phase partitioning and/or nature of one or more other compounds, or species. Additionally, the ORP in a WFGD absorber tank can influence the oxidation state of any selenium that is present in the absorber tank thereby impacting the ability of to control the emission of one or more selenium species. Generally speaking, an ORP of greater than about 300 mV in an ART tends to favor the formation of selenium (VI) species and/or compounds (e.g., selenate ions and/or compounds, etc.).

Additionally, the control of various Air Quality Control Systems (AQCS) are in need of optimization. As more and more power generation utilities are beginning to vary megawatt (MW) output, the boilers, SCRs, SNCRs, bag houses, ESPs and WFGD are being "asked" to fluctuate performance to respond to these changes in load. Thus, there is a need for various optimization programs that will permit for a more efficient use of ammonia, power input in the ESPs, limestone and/or lime injection into the WFGD or DFGDs and a potential for a higher quality gypsum byproduct.

Given the above, a need exists in the art for a system and/or method by which to control one or more process parameters of a combustion process so as to yield a favorable change in and/or permit the control of the ORP of a WFGD absorber tank thereby resulting in the ability to control one or more the downstream parameters so as to positively impact the ORP in the absorber tank of a WFGD unit, improve the operation of a WFGD unit, or improve, mitigate and/or control the emission of one or more species or compounds that occur from or downstream of a WFGD unit. Additionally a need exists to control the parameters of the various AQCS equipment to allow for one or more holistic optimization programs for one or more portions, of the totality, of an AQCS.

SUMMARY OF THE INVENTION

The present invention relates generally to the generation of steam via the use of a combustion process to produce heat and, in one embodiment, to a device, system and/or method that enables one to control one or more process parameters of a combustion process so as to yield at least one desirable change in at least one downstream parameter. In one embodiment, the present invention is directed to a system and/or method for controlling at least one process parameter of a combustion process so as to yield at least one desirable change in at least one downstream process parameter associated with one or more of a wet flue gas desulfurization (WFGD) unit, a particulate collection device and/or control of additives thereto and/or a nitrogen oxide control device and/or control of additives thereto and/or additives to the system. In another embodiment, the present invention is directed to a system and/or method for controlling at least two process parameters of a combustion process so as to yield at least one desirable change in at least one downstream process parameter associated with one or more of a wet flue gas desulfurization (WFGD) unit, a particulate collection device and/or control of additives thereto and/or a nitrogen oxide control device and/or control of additives thereto and/or additives to the system.

Accordingly, one aspect of the present invention is drawn to a method for optimizing a wet flue gas desulfurization unit, the method comprising the steps of: (I) measuring, analyzing and/or controlling at least one parameter selected from: (a) the type and/or amount of fuel to be combusted in the combustion process; (b) the oxidation air flow rate to the combustion process; (c) the ammonia slip across the selective catalytic reduction unit; (d) the nitrogen oxide output from a selective catalytic reduction unit; (e) the particulate control and/or capture device; (f) the mercury speciation in the flue gas and/or absorber tank; (g) the selenium speciation in the flue gas and/or absorber tank; (h) the chemistry in the flue gas and/or absorber tank of the WFGD; (i) the oxidation reduction potential of the absorber tank of the WFGD; (j) the amount of the suspended solids in the absorber tank of the wet flue gas desulfurization unit; (k) the analysis of the limestone and/or lime utilized in the wet flue gas desulfurization unit; (l) the amount of various reagents supplied to the wet flue gas desulfurization unit tower; (m) the $SO_2$ concentration at the flue gas inlet of the wet flue gas desulfurization unit; (n) the inlet opacity of the wet flue gas desulfurization unit; (o) the PI data from the wet flue gas desulfurization unit; (p) the amount of dissolved solids in the wet flue gas desulfurization unit; and/or (q) the relative saturation of the gypsum crystals in the wet flue gas desulfurization unit; (II) generating data from the at least one parameter of Step (I); (III) using the data generated in Step (II) to adjust at least one operational parameter selected from: (A) the operational wet flue gas desulfurization unit tower level; (B) the reagent feed flow to the wet flue gas desulfurization unit; (C) the oxidation air flow to the wet flue gas desulfurization unit; (D) the rate of absorber bleed from the wet flue gas desulfurization unit; (E) the liquid to gas ratio in the wet flue gas desulfurization unit tower; (F) the number of operating absorber recycle pumps in the wet flue gas desulfurization unit; (G) the dewatering operation parameters; (H) the ammonia feed rate to the selective catalytic reduction unit; (I) the gypsum purity; (J) the gypsum-related scale formation in the wet flue gas desulfurization unit absorber tower; (K) the parasitic power loss by the wet flue gas desulfurization unit equipment; (L) the oxidation-reduction potential in the absorber recirculation tank; (M) the wet flue gas desulfurization unit effluent stream waste water treatment parameters; (N) the $SO_2$ removal efficiency by the wet flue gas desulfurization unit; (O) the relative saturation of the gypsum crystals in the slurry; and/or (P) the total dissolved solids in the wet flue gas desulfurization unit.

In yet another aspect of the present invention, there is provided a method for optimizing a wet flue gas desulfurization unit, the method comprising the steps of: (i) measuring, analyzing and/or controlling at least one parameter in real time selected from: (a) the type and/or amount of fuel to be combusted in the combustion process; (b) the oxidation air flow rate to the combustion process; (c) the ammonia slip across the selective catalytic reduction unit; (d) the nitrogen oxide output from a selective catalytic reduction unit; (e) the particulate control and/or capture device; (f) the mercury speciation in the flue gas and/or absorber tank; (g) the selenium speciation in the flue gas and/or absorber tank; (h) the chemistry in the flue gas and/or absorber tank of the WFGD; (i) the oxidation reduction potential of the absorber tank of the WFGD; (j) the amount of the suspended solids in the absorber tank of the wet flue gas desulfurization unit; (k) the analysis of the limestone and/or lime utilized in the wet flue gas desulfurization unit; (l) the amount of various reagents supplied to the wet flue gas desulfurization unit tower; (m) the $SO_2$ concentration at the flue gas inlet of the wet flue gas desulfurization unit; (n) the inlet opacity of the wet flue gas desulfurization unit; (o) the PI data from the wet flue gas desulfurization unit; (p) the amount of dissolved solids in the wet flue gas desulfurization unit; and/or (q) the relative saturation of the gypsum crystals in the wet flue gas desulfurization unit; (ii) generating real-time data from the at least one parameter of Step (I); (iii) using the real-time data generated in Step (ii) to adjust at least one operational parameter selected from: (A) the operational wet flue gas desulfurization unit tower level; (B) the reagent feed flow to the wet flue gas desulfurization unit; (C) the oxidation air flow to the wet flue gas desulfurization unit; (D) the rate of absorber bleed from the wet flue gas desulfurization unit; (E) the liquid to gas ratio in the wet flue gas desulfurization unit tower; (F) the number of operating absorber recycle pumps in the wet flue gas desulfurization unit; (G) the dewatering operation parameters; (H) the ammonia feed rate to the selective catalytic reduction unit; (I) the gypsum purity; (J) the gypsum-related scale formation in the wet flue gas desulfurization unit absorber tower; (K) the parasitic power loss by the wet flue gas desulfurization unit equipment; (L) the oxidation-reduction potential in the absorber recirculation tank; (M) the wet flue gas desulfurization unit effluent stream waste water treatment parameters; (N) the $SO_2$ removal efficiency by the wet flue gas desulfurization unit; (O) the relative saturation of the gypsum crystals in the slurry; and/or (P) the total dissolved solids in the wet flue gas desulfurization unit.

In yet another aspect of the present invention, there is provided a method for optimizing a wet flue gas desulfurization unit, the method comprising the steps of: controlling, measuring and/or analyzing at least one process parameter of a combustion process and/or at least one combustion process air quality control system in order to yield at least one data set; using the at least one data set to effect a desirable change in at least one downstream process parameter associated with one or more of a wet flue gas desulfurization unit, a particulate collection device and/or a nitrogen oxide control device.

In yet another aspect of the present invention, there is provided a method for optimizing a wet flue gas desulfurization unit, the method comprising the steps of: controlling, measuring and/or analyzing at least two process parameters of a combustion process and/or at least one combustion process air quality control system in order to yield at least one data set; using the at least two data sets to effect a desirable change in at least one downstream process parameter associated with one or more of a wet flue gas desulfurization unit, a particulate collection device and/or a nitrogen oxide control device.

In yet another aspect of the present invention, there is provided a method for optimizing a wet flue gas desulfurization unit, the method comprising the steps of: measuring, analyzing and/or controlling at least one parameter selected from: (i) desulfurization tower load; (ii) oxidation air flow rate; (iii) one or more boiler parameters; (iv) one or more selective catalytic reduction unit parameters; and/or (v) one or more electrostatic precipitator parameters; generating data from the at least one parameter of the previous Step; and using the data generated in the previous Step to adjust at least one operational parameter selected from: (a) one or more gypsum production properties and/or parameters; (b) the oxidation-reduction potential in the absorber recirculation tank; (c) the pH of the absorber recirculation tank solution; (d) the concentration, type and/or speciation of one or more compounds and/or ions in the absorber recirculation tank solution; and/or (e) the concentration, type and/or speciation of one or more oxidizer compounds and/or ions in the absorber recirculation tank solution and/or the wet flue gas desulfurization unit.

The various features of novelty which characterize the invention are pointed out with particularity in the claims annexed to and forming a part of this disclosure. For a better understanding of the invention, its operating advantages and specific benefits attained by its uses, reference is made to the accompanying drawings and descriptive matter in which exemplary embodiments of the invention are illustrated.

DESCRIPTION OF THE INVENTION

The present invention relates generally to the generation of steam via the use of a combustion process to produce heat and, in one embodiment, to a device, system and/or method that enables one to control one or more process parameters of a combustion process so as to yield at least one desirable change in at least one downstream parameter. In one embodiment, the present invention is directed to a system and/or method for controlling at least one process parameter of a combustion process so as to yield at least one desirable change in at least one downstream process parameter associated with one or more of a wet flue gas desulfurization (WFGD) unit, a particulate collection device and/or control of additives thereto and/or a nitrogen oxide control device and/or control of additives thereto and/or additives to the system. In another embodiment, the present invention is directed to a system and/or method for controlling at least two process parameters of a combustion process so as to yield at least one desirable change in at least one downstream process parameter associated with one or more of a wet flue gas desulfurization (WFGD) unit, a particulate collection device and/or control of additives thereto and/or a nitrogen oxide control device and/or control of additives thereto and/or additives to the system.

In one embodiment, the present invention the system and/or method of the present invention includes controlling and/or monitoring one or more of: (i) desulfurization tower load; (ii) oxidation air flow rate; (iii) one or more boiler parameters; (iv) one or more selective catalytic reduction (SCR) unit parameters; and (v) one or more parameters of the particulate collection device (e.g., the electrostatic precipitator (ESP)).

Given the above, a more detailed discussion of each of the above parameters will be discussed herein below. Turning to parameter (i), in one embodiment the system and/or method of the present invention involves analyzing, controlling and/or monitoring the tower load of a desulfurization unit (e.g., a wet flue gas desulfurization unit (WFGD)) via analyzing, controlling and/or monitoring one or more of the megawatt load being generated by the boiler unit; the $SO_2$ removal rate; and/or the inlet $SO_2$ amount present at least one inlet to the desulfurization unit.

Turning to parameter (ii), in one embodiment the system and/or method of the present invention involves analyzing, controlling and/or monitoring the amount, flow rate and/or type of the oxidation air that is supplied to a desulfurization unit (e.g., a wet flue gas desulfurization unit (WFGD)). While not wishing to be bound to any one theory, it is believed that by analyzing, controlling and/or monitoring the amount, flow rate and/or type of the oxidation air that is supplied to a desulfurization unit it is possible to control the production of sulfite compounds and/or species in the flue gas as well as in the desulfurization unit. This in turn is believed to impact the formation of other strong oxidizers as sulfite ions are known to act as reducing agents in a flue gas and/or desulfurization unit environment. Furthermore, the production of sulfite ions and/or species can have an impact on the production and/or presence of any ozone that may occur due to the operation of any one or more particulate collection devices (e.g., an electrostatic precipitator). Additionally, via the control of the amount and/or concentration of various types of sulfite species and/or ions, it is possible to control the calcium sulfite to calcium sulfate conversion rate which in turn permits one to control the gypsum production rate and/or purity of the WFGD.

Turning to parameter (iii), in one embodiment the system and/or method of the present invention involves analyzing, controlling and/or monitoring various boiler parameters. Such parameters include, but are not limited to, fuel supply rate, oxidation air supply rate, overfire air supply rate, type of fuel, fuel composition, fuel type, fuel impurities, etc. Given the analysis, control and/or monitoring of one or more of the above noted boiler parameters, various resulting downstream parameters or downstream process parameters can be controlled. While not wishing to be bound to any one theory and/or downstream process parameters that can be controlled, it is then possible via the control of one or more of the above noted boiler parameters to impact the ORP in, for example, a recirculation tank of a wet scrubber (also referred to as an absorber recirculation tank or ART). This in turn permits the control and/or mitigation of various corrosion issues that occur when the ORP in an ART becomes undesirable. Additionally, the analysis, control and/or monitoring of one or more boiler parameters can permit the control of ash resistivity.

As used herein, "ash resistivity" refers to the resistivity of the ash to accept a charge. The ash resistivity affects the ability of the particulate collection device, and in particular, an electrostatic precipitator, to efficiently complete its assigned task (that is the collection of particulate material from a flue gas). Additionally, the boiler parameters also have an impact on the operating conditions of any SCR that might be utilized to remove nitrous oxides from the flue gas. Given the above, the boiler parameters can indirectly impact the amount of ozone that may be produced by an ESP as the boiler parameters impact the amount and/or type of ash that is produced by the combustion process. The ash type and/or amount in turn influences the operating conditions that are necessary in the ESP to collect said ash. For example, if an ESP has to operate at a high power and/or higher sparking rate in order to adequately collect the ash in the flue gas, such conditions can lead to an increase in the production of ozone in the flue gas.

While not wishing to be bound to any one theory, it is believed that an increase in the concentration (or amount) of ozone in the flue gas leads to an undesirable change in the ORP in an ART (this is of course in the case where the flue gas desulfurization unit is a WFGD). This is because ozone is a strong oxidizer. Thus, the boiler parameters indirectly impact the amount of ozone generated via the impact such parameters have on ash resistivity. This is true in most cases but may not generate and/or yield the same results and/or impact on ozone production and/or ESP parameters if one or more additives added to the coal prior to the coal being supplied to the burners and/or any additives are added to the boiler and/or flue gas stream upstream (i.e., the hot side) of the SCR.

Turning to parameter (iv), in one embodiment the system and/or method of the present invention involves analyzing, controlling and/or monitoring various SCR parameters. Such parameters include, but are not limited to, the ammonia slip across the selective catalytic reduction (SCR) unit and/or the nitrogen oxide output from a SCR. It is believed that such parameters can impact the ORP in the ART. In one embodiment, the control of various boiler parameters are more important in the control of the ORP in the ART than it is to control various SCR parameters. In another embodiment, it is more important to control the SCR parameters instead of the boiler parameters in order to achieve the desired ORP control. In yet another embodiment, the desired control of the ORP in the ART is achieved by controlling any various combination of at least one boiler parameter in combination with at least one SCR parameter.

Turning to parameter (v), in one embodiment the system and/or method of the present invention involves analyzing, controlling and/or monitoring various ESP parameters. As would be apparent to those of skill in the art, this factor applies only if there is an ESP present in the air quality control systems attached to the combustion process in question. In one embodiment, the ESP parameters that are analyzed, controlled and/or monitored include, but are not limited to, ESP power and/or ESP sparking rate.

As noted above, ESP power and/or ESP sparking rate is a function of ash resistivity. This is because it is necessary to increase either one or both of ESP power and/or ESP sparking rate to achieve a desired level of ash removal if the ash has a high resistivity to the acceptance of a charge. The higher the ESP power and/or ESP sparking rate, the higher the ozone production rate and/or concentration. This in turn leads to a higher ORP in the ART do to either the direct impact of an increase in the concentration of ozone or some chemical and/or species generated by ozone reacting with another species or compound present in the flue gas. The injection of $SO_3$, trona (i.e., trisodium hydrogendicarbonate which can also be written in its hydrated form as $Na_3(CO_3)(HCO_3).2H_2O$) and/or hydrated lime seems to impact the formation of ozone in the ESP. It should be noted that the term "trona" is to be broadly construed and is not solely limited to just the hydrated state detailed above.

While not wishing to be bound to any one theory, it is believed that the injection of one or more of the above compounds effects ash resistivity and thus impacts either positively or negatively the amount of ozone generated by the power and sparking in the ESP. As such, in one embodiment the present invention encompasses the analysis, control and/or monitoring of the type of materials injected into the flue gas stream to determine the impact of such compounds on ash resistivity. As noted above, an increase in ash resistivity can lead to an increase in ozone production because it becomes necessary to increase either one or both of ESP power and/or ESP sparking rate in order to achieve the desired level of ash removal as the ash becomes more resistive to accepting a charge. This in turn can, as noted above, result an undesired change in the ORP of an ART due to the presence of an increased amount of ozone and/or an increase in various reaction products formed due to the interaction of various flue gas constituents with the increased level of ozone.

Given the above, the one or more analyses, control measures, measurements and/or determinations of the various parameters listed above can permit the control and/or optimization of one or more of the following: (a) one or more gypsum production properties and/or parameters including, but no limited to, gypsum purity, gypsum moisture content and/or gypsum mass flow; (b) the oxidation-reduction potential (ORP) in the absorber recirculation tank (ART); and (c) the pH of the ART solution. The ORP in the Art can be measured, monitored and/or determined by the ORP in mV or a sensor designed to measure and/or monitor the oxidizer content in the ART solution. The ORP in turn can influence various parameters including, but not limited to, the aqueous species in the ART solution such as selenium, cobalt, manganese, mercury, arsenic, as well as potentially any other trace elements that might be in coal that might be regulated now or in the near future. Regarding the pH of the ART solution, the pH of this solution can be measured by various known methods including, but not limited to, titration, pH meters, etc.

In another embodiment, the system and/or method of the present invention includes controlling and/or monitoring one or more of: (I) the type and/or amount of fuel to be combusted in the combustion process (e.g., fossil fuel type such as coal type); (II) the oxidation air flow rate to the combustion process; (III) the ammonia slip across the selective catalytic reduction (SCR) unit, if present; (IV) the nitrogen oxide output from a SCR, if present; (V) the particulate control and/or capture device (e.g., electrostatic precipitator (ESP)) including, but not limited to, one or more particulate collection device operating parameters; the additives to the ESP system including, but not limited to, ash condition agents including but not limited to sulfur species; system additives injected for $SO_3$ mitigation; (VI) the mercury speciation in the flue gas and/or absorber tank; (VII) the selenium speciation in the flue gas and/or absorber tank; (VIII) the chemistry in the flue gas and/or absorber tank of the WFGD; (IX) the oxidation reduction potential (ORP) of the absorber tank of the WFGD; the pH within the absorber tank; (X) the amount of the suspended solids (SS) in the absorber tank of the WFGD; (XI) the analysis of the limestone and/or lime utilized in the WFGD; (XII) the amount of various reagents supplied to the WFGD tower; (XIII) the $SO_2$ concentration at the flue gas inlet of the WFGD; (XIV) the inlet opacity of the WFGD; and/or (XV) the PI data from the WFGD.

Given the above, a more detailed discussion of each of the above parameters will be discussed herein below. Turning to parameter (I), in one embodiment the system and/or method of the present invention involves analyzing, controlling and/or monitoring the type and/or amount of fuel to be combusted in the combustion process (e.g., fossil fuel type such as coal type). In the case where an analysis of this parameter is utilized the analysis of the fuel to be combusted can be accomplished by any one or more known analysis techniques including, but not limited to, gas chromatography, liquid chromatography, gas chromatography-mass spectroscopy (GC-MS), mass spectroscopy, NMR analysis, FTIR, flame analysis, etc. In another embodiment, the analysis of the fuel to be combusted can be accomplished by utilizing any two or more of the above-mentioned techniques. When utilized, the analysis of the fuel to be combusted can involve analyzing the heating value, the amount of phosphorus, hydrogen, chlorine, fluorine, sulfur, one or more heavy metals (e.g., mercury, cadmium, selenium, etc.), moisture content, ash content, carbon content, mineral content (e.g., pyrite).

Alternatively, the amount of sulfur and/or phosphorus in a combustion gas can be ascertained utilizing one or more sensors or probes designed to measure the amount of gas-phase sulfur and/or gas-phase phosphorus. Since such probes are known to those of skill in the art, a detailed discussion herein is omitted for the sake of brevity. As would be apparent to those of skill in the art, any probes and/or sensors utilized in connection with the various systems and/or methods of the present invention can be placed at one or more locations in a steam generation combustion process including, but not limited to, the boiler, the combustion zone of the boiler, the economizer, the air heater (if present), the SCR or SNCR (if present), the particulate control device (e.g., a ESP or bag house), and/or the WFGD. It should be noted that the above positions are exemplary in nature and the present invention is not limited to solely the above-listed locations. Rather, any location within a steam generation system can be utilized where any one more sensors, or probes, located therein yield at least one piece of useful data. Additionally, any of the analyses discussed herein can, if so possible, be accomplished in real-time if a suitable sensor, or probe, is available to measure and/or analyze the desired given parameter, or parameters.

Turning to parameter (II), in one embodiment the system and/or method of the present invention involves analyzing, controlling and/or monitoring the oxidation air flow rate to the combustion process. In this embodiment, such an analysis can be accomplished by the use of a flow meter or other system that permits one to ascertain the amount of oxidation air that is being supplied to a combustion process. Alternatively, a metering system can be utilized so as to permit one to determine the amount of oxidation air that is being supplied to a combustion process. In another embodiment, various other system and/or methods are known to those that permit the metering and/or measurement of a gas being supplied to a process and can be utilized herein to determine the amount of oxidation air being supplied to a combustion process. It should be noted that some combustion process might not utilize a discrete oxidation air supply. In this instance, the analyses of the amount of oxidation air being supplied to a combustion process would be omitted.

Turning to parameter (III), in one embodiment the system and/or method of the present invention involves analyzing, controlling and/or monitoring the ammonia slip across the selective catalytic reduction (SCR) unit, if so present. As would be known to those of skill in the emissions control arts, systems and/or methods for determining the amount ammonia slip across an SCR are known in the art and any such system and/or method can be utilized in conjunction with the present invention to obtain data relating to the amount of ammonia slip across the SCR. Since such systems and/or methods are known in the art, a detailed discussion herein is omitted for the sake of brevity.

Turning to parameter (IV), in one embodiment the system and/or method of the present invention involves analyzing, controlling and/or monitoring the nitrogen oxide output from a SCR, if present. As would be known to those of skill in the emissions control arts, systems and/or methods for determining the amount nitrogen in a gas are known in the art and any such system and/or method can be utilized in conjunction with the present invention to obtain data relating to the amount and/or concentration of nitrogen and/or nitrogen-containing compounds in a gas. Since such systems and/or methods are known in the art, a detailed discussion herein is omitted for the sake of brevity.

Turning to parameter (V), in one embodiment the system and/or method of the present invention involves analyzing, controlling and/or monitoring the operating parameters of one or more particulate control and/or capture devices (e.g., electrostatic precipitator (ESP)). Such operating parameters can include, but are not limited to, power input, spark rate. Such operating parameters also include additives to or upstream of the ESP, including but not limited to fly ash conditioning agents, including but not limited to injection of sulfur species Turning to parameter (VI), in one embodiment the system and/or method of the present invention involves analyzing, controlling and/or monitoring the mercury speciation in the flue gas and/or absorber tank. As would be known to those of skill in the emissions control arts, systems and/or methods for determining the type of mercury species in a flue gas are known in the art and any such system and/or method can be utilized in conjunction with the present invention to obtain data relating to the type, amount and/or concentration of various mercury species in a gas. Suitable methods can include, but are not limited to, titration, liquid chromatography, gas chromatography-mass spectroscopy (GC-MS), mass spectroscopy, NMR analysis, FTIR, and/or flame analysis. Since such systems and/or methods are known in the art, a detailed discussion herein is omitted for the sake of brevity.

Turning to parameter (VII), in one embodiment the system and/or method of the present invention involves analyzing, controlling and/or monitoring the selenium speciation in the flue gas and/or absorber tank. As would be known to those of skill in the emissions control arts, systems and/or methods for determining the type of selenium species in a flue gas are known in the art and any such system and/or method can be utilized in conjunction with the present invention to obtain data relating to the type, amount and/or concentration of various selenium species in a gas. Suitable methods can include, but are not limited to, titration, liquid chromatography, gas chromatography-mass spectroscopy (GC-MS), mass spectroscopy, NMR analysis, FTIR, and/or flame analysis. Since such systems and/or methods to accomplish same are known in the art, a detailed discussion herein is omitted for the sake of brevity.

Turning to parameter (VIII), in one embodiment the system and/or method of the present invention involves analyzing, controlling and/or monitoring the chemistry in the flue gas and/or absorber tank of the WFGD. As would be known to those of skill in the emissions control arts, systems and/or methods for determining various chemical and/or physical parameters in the solution of an absorber tank of a WFGD are known to those of skill in the art. Exemplary chemical and/or physical parameters that can be analyzed include, but are not limited to, the pH of the absorber tank solution, the specific gravity of the absorber tank solution, the viscosity of the absorber tank solution, the opacity of the absorber tank solution, the total suspended solids in the absorber tank solution, the recirculation rate of the solution in the absorber tank, and/or the present of one or more aqueous species in the absorber tank (e.g., persulfate species concentration and/or type, one or more oxidizer species and/or concentration, chloride concentration, fluoride concentration, calcium concentration, sulfur-oxygen compounds, sulfur-nitrogen compounds, magnesium species concentration and/or type, mercury concentration, selenium concentration and type). Here, as well as elsewhere in the specification and claims, the term "oxidizer" includes, but not limited to, persulfate, permanganate, manganate, ozone, hypochlorite, chlorate, nitric acid, iodine, bromine, chlorine, fluorine, or combinations of any two or more thereof. Here, as well as elsewhere in the specification and claims, the term "persulfate" is defined to include one or both of peroxodisulfate ions ($S_2O_8^{2-}$) or peroxomonosulfate ions ($SP_5^{2-}$). Accordingly, as used throughout the specification and claims the term "persulfate" includes both persulfate ions and other forms of the noted ionic compounds above regardless of whether such ions are bound in a chemical composition or in an ionic state because they are in solution.

Regarding the above one or more parameters to be measured and/or analyzed, suitable methods can include, but are not limited to, titration, liquid chromatography, gas chromatography-mass spectroscopy (GC-MS), mass spectroscopy, NMR analysis, FTIR, and/or flame analysis. Since such systems and/or methods to accomplish same are known in the art, a detailed discussion herein is omitted for the sake of brevity.

Turning to parameter (IX), in one embodiment the system and/or method of the present invention involves analyzing, controlling and/or monitoring the oxidation reduction potential (ORP) of the absorber tank of the WFGD. Such a determination of the ORP of the absorber tank solution can be accomplished by a variety of methods including, but not limited to, determining the concentration of various aqueous species (e.g., one or more oxidizer species concentration and/or type, persulfate species concentration and/or type, magnesium species concentration and/or type, chloride concentration, fluoride concentration, calcium concentration, sulfur-oxygen compounds, sulfur-nitrogen compounds, magnesium species concentration and/or type, mercury concentration, selenium concentration and type). Regarding the above one or more aqueous species to be measured and/or analyzed, suitable methods can include, but are not limited to, titration, liquid chromatography, gas chromatography-mass spectroscopy (GC-MS), mass spectroscopy, NMR analysis, FTIR, electrical measurement of the conductiveness of the absorber tank solution, oxidation reduction potential measurements, and/or flame analysis. Since such systems and/or methods to accomplish same are known in the art, a detailed discussion herein is omitted for the sake of brevity.

Turning to parameter (X), in one embodiment the system and/or method of the present invention involves analyzing, controlling and/or monitoring the suspended solids (SS), or even total suspended solids (TSS), in the absorber tank of the WFGD. Such measurements can be accomplished by a variety of known techniques and/or systems including, but not limited to, turbidity and/or opacity measurements, titration, etc.

Turning to parameter (XI), in one embodiment the system and/or method of the present invention involves analyzing, controlling and/or monitoring the limestone and/or lime utilized in the WFGD. Such an analysis can include, but is not limited to, a compositional analysis, the amount of limestone and/or lime being supplied to the WFGD via one or more techniques including, but not limited to, titration, liquid chromatography, gas chromatography-mass spectroscopy (GC-MS), mass spectroscopy, NMR analysis, FTIR, electrical measurement of the conductiveness of the absorber tank solution, oxidation reduction potential measurements, and/or flame analysis. Since such systems and/or methods to accomplish same are known in the art, a detailed discussion herein is omitted for the sake of brevity.

Turning to parameter (XII), in one embodiment the system and/or method of the present invention involves analyzing, controlling and/or monitoring the amount of various reagents supplied to the WFGD tower. Such reagents include, but are not limited to, water, pH buffer, reducing agents, oxidizing agents, organic acids). Such an analysis can include, but is not limited to, a compositional analysis, purity analysis, etc. supplied to a WFGD via one or more techniques including, but not limited to, titration, liquid chromatography, gas chromatography-mass spectroscopy (GC-MS), mass spectroscopy, NMR analysis, FTIR, electrical measurement of the conductiveness of the absorber tank solution, oxidation reduction potential measurements, and/or flame analysis. Since such systems and/or methods to accomplish same are known in the art, a detailed discussion herein is omitted for the sake of brevity.

Turning to parameter (XIII), in one embodiment the system and/or method of the present invention involves analyzing, controlling and/or monitoring the $SO_2$ concentration at the flue gas inlet of the WFGD. As would be known to those of skill in the emissions control arts, systems and/or methods for determining the amount $SO_2$ in a gas are known in the art and any such system and/or method can be utilized in conjunction with the present invention to obtain data relating to the amount and/or concentration of $SO_2$ in a gas. Since such systems and/or methods are known in the art, a detailed discussion herein is omitted for the sake of brevity.

Turning to parameter (XIV), in one embodiment the system and/or method of the present invention involves analyzing, controlling and/or monitoring the inlet opacity of the WFGD. Such an analysis can be accomplished by a variety of methods including, but not limited to, titration testing, turbidity measurements and/or opacity measurements. Turning to parameter (XV), in one embodiment the system and/or method of the present invention involves analyzing the PI data from the WFGD.

Additionally, as noted above, any of the analyses discussed herein can, if so possible, be accomplished in real-time if a suitable sensor, or probe, is available to measure and/or analyze the desired given parameter, or parameters.

In the case where real time data is desired at least one computer and/or computational system can be utilized in conjunction with the present invention. Such computer systems and/or computational devices are known to those of skill in the art and as such a discussion herein is omitted for the sake of brevity.

Given the above, the one or more analyses, control measures, measurements and/or determinations of the various parameters listed above can permit the control and/or optimization of one or more of the following: (A) operational WFGD tower level; (B) reagent feed flow to the WFGD; (C) oxidation air flow to the WFGD; (D) rate of absorber bleed from the WFGD; (E) liquid to gas ratio in the WFGD tower; (F) the number of operating absorber recycle pumps in the WFGD; (G) dewatering (hydroclone) operation parameters; (H) ammonia feed rate to the SCR (if present); (I) the number of ESP feeds in operation in a WFGD; (J) gypsum purity; (K) gypsum-related scale formation in the WFGD absorber tower; (L) parasitic power loss by the WFGD equipment; (M) WFGD effluent stream waste water treatment parameters; and (N)$SO_2$ removal efficiency by the WFGD.

This system and/or method of the present invention can, in one embodiment, achieve for a more responsive control system which will allow the WFGD system to function better during times of non-steady state operation by the boiler. More and more, coal fired utilities are swinging boiler load to allow for steady power grid operation. A more responsive control system may lead to better tower chemistry thereby achieving an improvement in $SO_2$ removal efficiency.

As an example of one such non-limiting parameter and/or operating condition that can be measured and therefore controlled is the ORP level of the solution in an absorber tank of a WFGD. Controlling ORP to a pre-determined range and steady state condition can help mitigate corrosion potential in the tower as well as to control elemental vapor phase mercury formation and reemission. An optimization program that will help to control the SCR and ESP parameters may lead to less ammonia injection and less power requirement by the ESP. An optimization program has the potential to mitigate parasitic power loss of the equipment.

In one embodiment, the system and/or method of the present invention involves flue gas testing that is accomplished by continuous Fourier Transform Infrared Spectroscopy (FTIR) monitoring for all gas species and carbon trap mercury monitoring across the SCR and GEMS mercury testing at the SCR inlet during baseline testing and SCR testing weeks. Stack mercury analysis will be performed using sorbent traps in the stack during baseline testing. Chemical analysis of the absorber slurry will consist of speciated mercury, selenium and ICP-MS. Corrosion testing will also be conducted in isolated buckets wherein metal samples and Electrical Resistance (ER) probes would contact the process slurry. This testing will afford the opportunity for B&W to optimize the performance of these units.

As noted above, in one embodiment the present invention relates generally to the field of emissions control and, in particular to a new and useful method and/or system by which to control various types of corrosion and/or precipitation issues in at least a portion of a wet flue gas desulfurization (WFGD) scrubber system. In one embodiment, the method and/or system of the present invention relies on the supply of at least one reducing agent to the slurry of a wet flue gas desulfurization scrubber to lower the oxidation reduction potential in the absorber slurry contained within the wet flue gas desulfurization scrubber. In still another embodiment, the method and/or system of the present invention control the oxidation-reduction potential in at least one bleed stream of an absorber slurry, filtrate, and/or solution from a wet flue gas desulfurization scrubber.

As discussed above, it has been determined that a high oxidation-reduction potential (ORP) and concentration of one or more oxidizer compounds and/or species (e.g., persulfate, permanganate, manganate, ozone, hypochlorite, chlorate, nitric acid, iodine, bromine, chlorine, fluorine, or combinations of any two or more thereof) in a wet scrubber's absorber recirculation tank (ART) causes precipitation of soluble manganese. While not wishing to be bound to any one theory, it is believed manganese dioxide precipitate ($MnO_2$) settling on the walls of the ART can create a galvanic cell leading to corrosion, or further enhancing the circumstances that cause corrosion. While not wishing to be bound to any one solution, one possible method to control, reduce and/or mitigate the ORP in an ART is to reduce the ORP by controlling, eliminating and/or reducing the concentration, or amount, of one or more oxidizer compounds and/or species (e.g., persulfate, permanganate, manganate, ozone, hypochlorite, chlorate, nitric acid, iodine, bromine, chlorine, fluorine, or combinations of any two or more thereof—in the form of ions, etc.) that exist in, or are formed in, the ART of a WFGD. While the present invention is described in terms of corrosion that occurs in an ART formed from Alloy 2205 (UNS S32205, a duplex stainless steel alloy), the present invention is not limited thereto. Rather, corrosion can and does occur in a wide range of iron-based alloys and as such, the present invention applies to any situation where the ORP needs to be controlled in order to reduce, control and/or mitigate the corrosive nature of the environment in an ART.

In still another embodiment, the present invention further includes the use of surplus oxidation air, regardless of where such surplus is generated, as a manner by which to control the various chemical properties of one or more aqueous-based solutions or liquids. This embodiment of the present invention can be achieved by supplying a desired amount of surplus oxidation air to one or more tanks containing any type of desired aqueous-based or liquid solutions via a least one supply method which include, but are not limited to, sparging, bubblers, etc.

In still yet another embodiment, the present invention permits the control of sparking in a particulate removal device (e.g., an electrostatic precipitator—ESP) which in turn permits the control of various factors that influence oxidizer formation. While not wishing to be bound to any one theory, one exemplary manner by which the ORP in an ART increases is due to the formation of ozone. Ozone formation can be traced to, among other things, an increase in sparking in an ESP. To prevent, control and/or mitigate the amount of sparking in an ESP an additive such as $SO_3$ and/or trona can be added upstream of an ESP. Upon the addition of $SO_3$ and/or trona a decrease in ozone formation is observed due to a decrease in the amount of sparking in the ESP. This in turn allows for a more favorable ORP in the ART which in turn results in the ability to favorably control the nature of various aqueous species in the ART solution. Such species that can be controlled include, but are not limited to, oxidizer species concentration and type (e.g., persulfate species concentration and/or type), magnesium species concentration and/or type, chloride concentration, fluoride concentration, calcium concentration, sulfur-oxygen compounds, sulfur-nitrogen compounds, magnesium species concentration and/or type, mercury concentration, selenium concentration and type, or any two or more thereof.

One non-limiting example of the present invention was performed via field testing at the Detroit Edison (DTE) Monroe Power Plant in November and December of 2012. This testing was conducted to examine the effects of process changes upon wet flue gas desulfurization (WFGD) chemistry. Accordingly to one embodiment of the present invention, a parametric test plan to change coals, electrostatic precipitator (ESP) operation, ammonia slip to the SCR, WFGD oxidation air injection loading and the total suspended solids (TSS) of the WFGD absorber recirculation tank (ART). Various parameters where measured and the results thereof are detailed in Tables 1 and 2 below. Of the parameters tested, modification of the $SO_3$ injection to the ESP had the most pronounced impact on WFGD absorber and effluent (WFGD bleed) stream chemistry.

The ESP at DTE Monroe is designed for operation with a mid-sulfur coal, 3.0 lbs/mBTU. DTE Monroe has switched to burning a lower-sulfur coal blend, with different physical characteristics, than that for which the air quality control system (AQCS) had been designed. $SO_3$ was injected into the ductwork upstream of the ESPs as a fly ash conditioning agent to improve ESP removal on the current coal. During testing at DTE Monroe, $SO_3$ injection prior to the ESP was shut off. One effect of the $SO_3$ injection in combination with the coal burned is that, for this system, one observes a decrease in spark rate within the ESP than would be expected without injection. Accordingly, when the $SO_3$ injection was turned off, ESP spark rate increased. Such an increase in spark rate likely causes an increase in ozone production within the WFGD, thereby increasing the concentration of downstream oxidizer(s). Other potential routes for increased oxidizer concentration within the flue gas may also be traced back to this increased sparking. Within a short period of time after shutting off the $SO_3$ injection, the ORP in the WFGD absorber reacting tank slurry increased by approximately 300 mV, changing the oxidation state and phase partitioning of many slurry constituents therein.

After the $SO_3$ injection was restarted, the ORP of the WFGD slurry slowly returned to the lower levels that had been exhibited during baseline testing. This return to baseline conditions occurred slowly and with a pattern consistent with residence time decay. None of the other parameters tested exhibited such a pronounced and dramatic change in scrubber chemistry. This parametric change of turning the $SO_3$ to the ESP has since been replicated in both operating absorber towers (Units 3 & 4) at DTE Monroe at least twice, all times exhibiting a similar response to the change. Accordingly, given the above, in one embodiment the present invention seeks to utilize $SO_3$ and/or trona injection prior to an ESP to effect a desirable change in the ORP of an ART of a WFGD.

TABLE 1

| Date/Time | Grab Sample ORP (mV) | pH | DO (mg/L) | Conductivity (mS) | $S_2O_8$ by Iodometry (mg/L) | pH | DCS ORP (mV) | Dissolved Hg (µg/L) | Total Hg (µg/L) | Selenite (µg/L) | Selenate (µg/L) |
|---|---|---|---|---|---|---|---|---|---|---|---|
| Nov. 15, 2012 14:35 | 243.70 | 5.40 | 0.00 | 0.00 | 0.00 | 0.00 | N/A | 3.83 | 473.80 | 76.98 | 73.01 |
| Nov. 16, 2012 12:42 | 246.20 | 5.43 | 5.81 | 53.40 | 107.50 | 0.00 | N/A | 5.83 | 501.88 | 9.46 | 9.35 |
| Nov. 17, 2012 10:45 | 235.70 | 5.56 | 5.05 | 33.80 | 115.20 | 0.00 | N/A | 7.96 | 558.55 | 159.83 | 73.41 |
| Nov. 18, 2012 10:18 | 233.70 | 5.51 | 4.93 | 40.10 | 109.44 | 0.00 | N/A | 12.20 | 540.34 | 77.33 | 76.33 |
| Nov. 19, 2012 10:20 | 245.60 | 5.56 | 5.20 | 38.90 | 109.44 | 0.00 | N/A | 10.60 | 533.04 | 22.56 | 83.99 |
| Nov. 26, 2012 10:21 | 273.80 | 5.82 | 4.79 | 28.86 | 124.80 | 0.00 | N/A | 5.54 | 665.46 | 251.48 | 82.70 |
| Nov. 27, 2012 9:59 | 266.90 | 5.78 | 5.62 | 32.80 | 115.20 | 5.75 | 249.00 | 9.73 | 585.70 | 265.09 | 933.27 |
| Nov. 28, 2012 10:08 | 277.00 | 5.71 | 4.89 | 34.20 | 145.92 | 5.75 | 251.00 | 5.93 | 689.05 | 99.00 | 942.78 |
| Nov. 29, 2012 9:28 | 279.40 | 5.64 | 4.42 | 33.60 | 126.72 | 5.72 | 250.00 | 7.27 | 613.27 | 246.27 | 1030.57 |
| Nov. 30, 2012 8:50 | 298.90 | 5.61 | 4.21 | 33.00 | 167.00 | 5.72 | 247.00 | 8.40 | 594.52 | 69.27 | 995.66 |
| Dec. 1, 2012 9:27 | 303.90 | 5.47 | 4.90 | 29.50 | 136.32 | 5.52 | 248.00 | 16.40 | 579.29 | 605.72 | 864.53 |
| Dec. 2, 2012 9:35 | 301.90 | 5.11 | 4.46 | 34.30 | 117.12 | 5.15 | 248.00 | 23.50 | 559.98 | 431.29 | 882.29 |
| Dec. 3, 2012 9:50 | 305.00 | 5.57 | 4.44 | 33.40 | 142.08 | 5.58 | 239.00 | 16.90 | 611.64 | 117.06 | 890.55 |
| Dec. 4, 2012 9:10 | 289.50 | 5.43 | 4.71 | 40.70 | 140.16 | 5.66 | 238.00 | 17.90 | 631.47 | 58.91 | 802.47 |
| Dec. 5, 2012 9:43 | 298.30 | 5.55 | 4.71 | 32.90 | 145.92 | 5.72 | 246.00 | 7.42 | 548.42 | 69.93 | 825.34 |
| Dec. 6, 2012 9:02 | 391.10 | 5.48 | 6.04 | 36.30 | 190.08 | 5.58 | 244.00 | 1.57 | 604.95 | 31.68 | 854.26 |
| Dec. 7, 2012 8:49 | 312.10 | 5.82 | 5.98 | 28.12 | 172.80 | 5.87 | 235.00 | 2.82 | 516.64 | 0.00 | 950.24 |
| Dec. 10, 2012 11:34 | 283.00 | 5.98 | 5.72 | 30.30 | 192.00 | 5.73 | 199.00 | 0.97 | 518.21 | 68.06 | 984.01 |
| Dec. 10, 2012 14:18 | 276.50 | 5.97 | 5.16 | 29.20 | 176.64 | 5.76 | 203.00 | 1.74 | 440.27 | 29.60 | 953.80 |
| Dec. 11, 2012 9:46 | 265.60 | 5.82 | 5.50 | 27.91 | 161.28 | 5.71 | 204.00 | 3.24 | 411.71 | 0.00 | 718.18 |

TABLE 1-continued

| Date/Time | Grab Sample ORP (mV) | pH | DO (mg/L) | Conductivity (mS) | S₂O₈ by Iodometry (mg/L) | pH | DCS ORP (mV) | Dissolved Hg (µg/L) | Total Hg (µg/L) | Selenite (µg/L) | Selenate (µg/L) |
|---|---|---|---|---|---|---|---|---|---|---|---|
| Dec. 11, 2012 12:04 | 263.10 | 5.91 | 5.36 | 26.76 | 159.36 | 5.69 | 197.00 | 0.78 | 320.22 | 621.20 | 710.93 |
| Dec. 11, 2012 16:02 | 272.40 | 5.84 | 5.36 | 23.98 | 140.16 | 5.62 | 214.00 | 1.54 | 376.82 | 607.40 | 693.59 |
| Dec. 12, 2012 9:09 | 236.90 | 6.08 | 5.69 | 18.74 | 144.00 | 5.92 | 193.00 | 0.56 | 291.39 | 565.78 | 369.53 |
| Dec. 12, 2012 12:24 | 238.50 | 6.01 | 5.47 | 20.07 | 174.72 | 5.82 | 194.00 | 0.47 | 319.13 | 588.50 | 343.22 |
| Dec. 12, 2012 14:09 | 248.50 | 5.83 | 5.33 | 19.77 | 192.00 | 5.79 | 187.00 | 0.69 | 325.57 | 657.16 | 344.06 |
| Dec. 13, 2012 9:24 | 249.60 | 5.98 | 5.85 | 20.78 | 174.72 | 5.69 | 197.00 | 1.29 | 0.83 | 686.95 | 345.52 |
| Dec. 13, 2012 11:38 | 245.20 | 5.96 | 5.70 | 23.00 | 186.24 | 5.70 | 191.00 | 0.82 | 285.02 | 672.70 | 363.64 |
| Dec. 13, 2012 13:39 | 250.00 | 5.79 | 5.03 | 25.26 | 174.12 | 5.67 | 196.00 | 1.62 | 394.50 | 571.96 | 371.59 |
| Dec. 14, 2012 8:26 | 226.10 | 5.75 | 5.25 | 42.70 | 165.12 | 5.82 | 174.00 | 1.21 | 417.07 | 429.11 | 332.80 |
| Dec. 14, 2012 11:32 | 236.50 | 5.94 | 5.49 | 45.00 | 182.40 | 5.73 | 178.00 | 1.64 | 419.78 | 364.70 | 307.97 |
| Dec. 14, 2012 16:15 | 215.10 | 5.82 | 5.54 | 524.00 | 196.20 | 5.61 | 193.00 | 1.86 | 457.41 | 368.67 | 339.61 |

TABLE 2

| Date/Time | Grab Sample ORP (mV) | pH | DO (mg/L) | Conductivity (mS) | S₂O₈ by Iodometry (mg/L) | pH | DCS ORP (mV) | Dissolved Hg (µg/L) | Total Hg (µg/L) | Selenite (µg/L) | Selenate (µg/L) |
|---|---|---|---|---|---|---|---|---|---|---|---|
| Nov. 15, 2012 14:31 | 295.00 | 4.95 | 4.90 | 0.00 | 0.00 | 0.00 | N/A | 4.60 | 372.00 | 673.95 | 49.81 |
| Nov. 16, 2012 12:22 | 275.30 | 5.34 | 6.21 | 39.60 | 96.00 | 0.00 | N/A | 2.97 | 404.00 | 780.82 | 54.52 |
| Nov. 16, 2012 15:42 | 255.50 | 5.12 | 5.60 | 52.50 | 130.60 | 0.00 | N/A | 4.61 | 406.00 | 793.68 | 62.78 |
| Nov. 17, 2012 12:57 | 260.80 | 5.68 | 5.98 | 31.70 | 105.60 | 0.00 | N/A | 5.26 | 434.00 | 901.84 | 60.18 |
| Nov. 17, 2012 15:15 | 257.20 | 5.40 | 9.35 | 31.30 | 96.00 | 0.00 | N/A | 0.00 | 418.00 | 511.40 | 88.57 |
| Nov. 18, 2012 9:26 | 246.90 | 5.31 | 5.72 | 34.20 | 109.44 | 0.00 | N/A | 7.50 | 445.00 | 851.21 | 64.96 |
| Nov. 18, 2012 12:46 | 254.10 | 5.20 | 5.70 | 33.60 | 97.92 | 0.00 | N/A | 7.53 | 462.00 | 800.51 | 63.48 |
| Nov. 18, 2012 15:28 | 276.90 | 5.21 | 5.61 | 33.10 | 97.92 | 0.00 | N/A | 9.20 | 447.00 | 788.90 | 67.89 |
| Nov. 19, 2012 9:44 | 249.80 | 5.49 | 5.75 | 33.00 | 94.08 | 0.00 | N/A | 6.16 | 456.00 | 789.18 | 64.15 |
| Nov. 19, 2012 13:25 | 256.70 | 5.67 | 5.71 | 31.10 | 72.00 | 0.00 | N/A | 12.40 | 458.00 | 753.51 | 56.41 |
| Nov. 19, 2012 15:18 | 252.90 | 5.59 | 5.99 | 30.90 | 129.60 | 0.00 | N/A | 1.48 | 420.00 | 766.59 | 53.76 |
| Nov. 26, 2012 11:08 | 557.20 | 5.66 | 4.63 | 24.11 | 357.12 | 0.00 | N/A | 297.00 | 436.00 | 0.00 | 3259.90 |
| Nov. 26, 2012 13:23 | 531-557 | 5.59 | 4.92 | 24.45 | 458.90 | 5.64 | 524.00 | 335.00 | 466.00 | 0.00 | 3199.28 |
| Nov. 26, 2012 15:26 | 546.90 | 5.71 | 4.75 | 24.88 | 403.20 | 5.63 | 525.00 | 322.00 | 446.00 | 0.00 | 3456.03 |
| Nov. 27, 2012 9:03 | 564.30 | 5.42 | 5.24 | 22.18 | 328.32 | 5.58 | 513.00 | 334.00 | 437.00 | 0.00 | 3339.24 |
| Nov. 27, 2012 12:42 | 547.00 | 5.55 | 4.87 | 27.60 | 378.24 | 5.62 | 520.00 | 333.00 | 411.00 | 0.00 | 3322.38 |
| Nov. 27, 2012 16:14 | 548.00 | 5.55 | 4.90 | 28.56 | 359.04 | 5.53 | 519.00 | 372.00 | 477.00 | 0.00 | 3511.92 |
| Nov. 28, 2012 9:27 | 548.00 | 5.65 | 4.75 | 32.00 | 366.72 | 5.52 | 519.00 | 391.00 | 499.00 | 0.00 | 4547.54 |
| Nov. 28, 2012 13:35 | 564.00 | 5.53 | 5.36 | 24.60 | 364.80 | 5.54 | 523.00 | 408.00 | 528.00 | 0.00 | 4076.00 |
| Nov. 28, 2012 15:35 | 526.00 | 5.67 | 5.27 | 32.40 | 345.60 | 5.44 | 491.00 | 414.00 | 483.00 | 0.00 | 3776.43 |
| Nov. 29, 2012 10:09 | 570.60 | 5.41 | 5.15 | 26.87 | 357.12 | 5.55 | 540.00 | 384.00 | 493.00 | 0.00 | 3849.11 |
| Nov. 29, 2012 13:00 | 534.90 | 5.61 | 6.36 | 24.95 | 351.36 | 5.75 | 511.00 | 401.00 | 465.00 | 0.00 | 3950.23 |

TABLE 2-continued

| Date/Time | Grab Sample ORP (mV) | pH | DO (mg/L) | Conductivity (mS) | $S_2O_8$ by Iodometry (mg/L) | pH | DCS ORP (mV) | Dissolved Hg (μg/L) | Total Hg (μg/L) | Selenite (μg/L) | Selenate (μg/L) |
|---|---|---|---|---|---|---|---|---|---|---|---|
| Nov. 29, 2012 15:30 | 549.00 | 5.45 | 4.99 | 32.40 | 334.08 | 5.51 | 537.00 | 396.00 | 514.00 | 0.00 | 3896.06 |
| Nov. 30, 2012 9:21 | 520.30 | 5.37 | 5.21 | 33.00 | 362.88 | 5.66 | 505.00 | 325.00 | 408.00 | 0.00 | 2613.99 |
| Nov. 30, 2012 14:06 | 494.00 | 5.65 | 4.88 | 0.00 | 343.68 | 5.72 | 472.00 | 269.00 | 405.00 | 0.00 | 2258.24 |
| Nov. 30, 2012 15:47 | 522.00 | 5.62 | 4.62 | 34.60 | 339.84 | 5.74 | 457.00 | 278.00 | 382.00 | 0.00 | 2153.89 |
| Dec. 1, 2012 8:51 | 542.00 | 5.48 | 4.96 | 24.81 | 389.76 | 5.65 | 513.00 | 219.00 | 322.00 | 0.00 | 2448.43 |
| Dec. 1, 2012 11:50 | 511.00 | 5.65 | 5.23 | 25.60 | 418.56 | 5.67 | 493.00 | 206.00 | 351.00 | 0.00 | 2456.52 |
| Dec. 1, 2012 14:22 | 520.20 | 5.60 | 4.94 | 24.65 | 397.44 | 5.74 | 504.00 | 197.00 | 320.00 | 0.00 | 2352.68 |
| Dec. 2, 2012 9:05 | 527.00 | 5.72 | 5.22 | 28.22 | 405.12 | 0.00 | 450.00 | 240.00 | 355.00 | 0.00 | 2613.65 |
| Dec. 2, 2012 14:30 | 509.50 | 5.68 | 4.85 | 27.42 | 418.56 | 5.83 | 497.00 | 220.00 | 354.00 | 0.00 | 2516.77 |
| Dec. 2, 2012 16:00 | 505.10 | 5.69 | 5.14 | 27.10 | 455.04 | 5.84 | 495.00 | 226.00 | 330.00 | 0.00 | 2465.82 |
| Dec. 3, 2012 10:22 | 508.80 | 5.61 | 4.99 | 25.87 | 472.32 | 5.79 | 511.00 | 224.00 | 360.00 | 0.00 | 2389.62 |
| Dec. 3, 2012 13:40 | 510.90 | 5.40 | 5.72 | 35.10 | 456.96 | 5.76 | 510.00 | 235.00 | 349.00 | 0.00 | 2362.08 |
| Dec. 3, 2012 15:40 | 513.10 | 5.53 | 4.81 | 33.80 | 460.80 | 5.77 | 511.00 | 214.00 | 346.00 | 6.69 | 2330.85 |
| Dec. 4, 2012 9:47 | 522.10 | 5.54 | 4.89 | 31.40 | 458.88 | 5.78 | 511.00 | 205.00 | 302.00 | 10.04 | 2210.91 |
| Dec. 4, 2012 13:45 | 513.00 | 5.79 | 5.46 | 31.60 | 470.40 | 5.84 | 502.00 | 212.00 | 309.00 | 0.00 | 2260.63 |
| Dec. 4, 2012 15:22 | 519.40 | 5.49 | 5.10 | 30.80 | 470.40 | 5.65 | 508.00 | 192.00 | 328.00 | 0.00 | 2215.08 |
| Dec. 5, 2012 10:00 | 527.30 | 5.45 | 4.62 | 24.94 | 464.64 | 5.63 | 536.00 | 188.00 | 300.00 | 0.00 | 2336.88 |
| Dec. 5, 2012 13:50 | 579.20 | 5.20 | 5.00 | 24.24 | 399.36 | 5.42 | 553.00 | 84.20 | 281.00 | 0.00 | 2371.02 |
| Dec. 5, 2012 16:55 | 534.40 | 5.38 | 5.23 | 28.85 | 412.80 | 5.36 | 561.00 | 136.00 | 298.00 | 0.00 | 2466.75 |
| Dec. 6, 2012 9:24 | 579.60 | 5.25 | 5.19 | 24.09 | 416.60 | 5.46 | 556.00 | 110.00 | 316.00 | 0.00 | 3345.74 |
| Dec. 6, 2012 11:41 | 531.30 | 5.52 | 5.46 | 24.48 | 444.48 | 5.45 | 557.00 | 119.00 | 338.00 | 0.00 | 3568.89 |
| Dec. 6, 2012 16:45 | 560.10 | 5.56 | 5.56 | 22.66 | 359.04 | 5.50 | 560.00 | 148.00 | 329.00 | 0.00 | 3394.87 |
| Dec. 7, 2012 9:16 | 600.20 | 5.37 | 5.32 | 22.80 | 359.04 | 5.35 | 575.00 | 193.00 | 281.00 | 0.00 | 3571.63 |
| Dec. 7, 2012 11:23 | 632.10 | 5.32 | 5.82 | 22.87 | 353.28 | 5.25 | 575.00 | 219.00 | 348.00 | 0.00 | 3711.37 |
| Dec. 7, 2012 12:45 | 627.20 | 5.32 | 5.16 | 27.60 | 349.44 | 5.28 | 572.00 | 190.00 | 315.00 | 0.00 | 3853.27 |
| Dec. 13, 2012 9:46 | 337.80 | 7.35 | 8.85 | 13.38 | 136.32 | 7.77 | 350.00 | 26.80 | 144.00 | 77.98 | 1698.63 |
| Dec. 14, 2012 8:40 | 246.30 | 6.52 | 6.31 | 20.40 | 307.20 | 6.53 | 463.00 | 2.54 | 131.00 | 316.49 | 1942.57 |

In one embodiment, the present invention permits control of various compounds and/or species in the ART of a WFGD which in turn can impact on the amount of total dissolved solids, selenite and/or selenite, mercury, and/or boron in an effluent stream of a WFGD.

In another embodiment, the present invention is directed to a method of controlling one or more upstream parameters so as to control the oxidation-reduction potential (ORP) in an absorber recirculation tank (ART). In one embodiment, it is desirable to control both the pH of the ART as well as the ORP therein. While not wishing to be bound to any one theory, in one embodiment the present invention is directed to controlling one or more upstream parameters so as to impact the pH and ORP in an ART. In one embodiment, it is desirable to achieve a pH of less than about 7, less than about 6.5, or even less than about 6 while at the same time controlling various factors that impact on the ORP (e.g., ESP sparking, the type and/or concentration of one or more oxidizers, etc.) so that the ORP is less than about 500 mV, less than about 450 mV, less than about 400 mV, less than about 350 mV, or even less than about 300 mV. Here, as well as elsewhere in the specification and claims, individual numerical values can be combined to form additional and/or non-disclosed ranges. As would be appreciated by those of skill in the art, oxidation-reduction potential when measured at a pH of about 7 can generally range from a low of −0.8 V to a high of 1.2 V. It should also be noted that pH can influence the oxidation-reduction potential number. As such, the above range generally applies to the typical oxidation-reduction potential range when measured at pH 7. At other pHs different broad ranges could apply.

Accordingly, in another embodiment the present invention relates to one or more methods by which to control the ORP in an ART so as to reduce same. The reduction of the ORP in an ART can, in one embodiment, result in the formation of more desirable species and/or forms of one or more metals including, but not limited to, selenium, mercury, magnesium, cobalt, etc. As a non-limiting example, when the ORP in an ART is less than about 500 mV, less than about 450 mV, less than about 400 mV, less than about 350 mV, or even less than about 300 mV, the amount of selenium (IV) tends to be higher than when the ORP is above 500 mV. As an example, at an ORP of more than about 400 mV the amount of selenium (VI) tends to be much greater than the amount of selenium (IV) in an ART slurry and/or solution. Additionally, as the ORP in an ART slurry and/or solution further decreases below 400 mV (e.g., below about 350 mV, or below about 325 mV, or even below 300 mV), the amount of selenium (VI) decreases and the amount of selenium (IV) increases. While not wishing to be bound to any one theory, it is believed that when the ORP in an ART slurry and/or solution is above 500 mV almost all, if not all, of the selenium present in the ART slurry and/or solution is in the form of selenium (VI) which in turn facilitates, or highly favors, the formation of various aqueous soluble selenium compounds and/or ions (e.g., selenate ions). This in turn results in selenium being undesirably discharged from one or more aqueous effluent streams and may, in the future, require additional emissions control technologies to reduce the amount of selenium emitted in various effluent streams. Thus, in various situations, it is desirable to control the ORP in an ART to thereby achieve at least some level of control over selenium speciation and in turn mitigate, reduce and/or control the concentration of various aqueous soluble selenium compounds and/or ions in various aqueous effluent streams. Given this, a reduction in the ORP in an ART below about 500 mV, below about 450 mV, below about 400 mV, below about 350 mV, or even below about 300 mV, results in at least some reduction, mitigation and/or control of the amount of aqueous soluble selenium compounds and/or ions that are emitted from one or more effluent streams from a WFGD. Furthermore, any additional reduction in the ORP in an ART below 300 mV can result in even more selenium being speciated as selenium (IV) and result in a further reduction, mitigation and control of aqueous soluble selenium compounds and/or ions in one effluent streams. Here, as well as elsewhere in the specification and claims, individual numerical values can be combined to form additional and/or non-disclosed ranges.

It should be noted that in some embodiments of the present invention it might be more desirable to mitigate, control and/or reduce the emission of one or more compounds and/or ions even if such mitigation, control and/or reduction causes an increase in the emission of one or more different compounds, ions and/or pollutants. In such cases, a second and different technology can be used to mitigate, reduce and/or control the emission of any such different compound, ion and/or pollutant which, although undesirable, is emitted at an increased level. As a non-limiting example, one might desire to have a higher degree of mitigation, reduction and/or control over selenium speciation. However, this may result in an undesirable increase in the emission of one or more other compounds, ions and/or pollutants (e.g., mercury reemission). Accordingly, rather than trying to achieve an ORP in the ART that impacts favorable on every compound, ion and/or pollutant that one is seeking to mitigate, reduce and/or control, in some instances it could be, and typically is, desirable to utilize one or more other emissions control technologies to deal with any other compounds, ions and/or pollutants that may be emitted at an undesirable and/or increased amount (e.g., mercury reemission). In still another embodiment, it might be desirable to control, reduce and/or mitigate the type, amount and/or speciation of various other compounds, ions and/or pollutants via control of the ORP in an ART that will be unfavorable to selenium speciation while using a different emissions control technology to deal with any selenium that is emitted from one or more aqueous effluent streams or other emissions points. In summation, it might be necessary to "choose" a given ORP in an ART with the knowledge that by doing so one might selectively control a certain portion of total compounds, ions and/or pollutants that are sought to be controlled. Regarding the compounds, ions and/or pollutants that are not controlled via the selection of a favorable ORP in an ART for such a control process, these compounds, ions and/or pollutants could be controlled by one or more other emissions control technologies that do not solely depend on the ORP value in the ART.

In still another embodiment, when it is desired to control selenium speciation as well as mercury speciation, the present invention relates to a method that permits one to control the oxidation-reduction potential (ORP) in an ART so as to be in the range of about 300 mV to about 500 mV. While not wishing to be bound to any one theory, it is believed that at the typical pHs present in an ART when the ORP in such an ART is in a range of about 300 mV to about 500 mV, mercury ions (e.g., in the form of mercury (II) and/or mercury (IV)) are the predominant species of mercury present in an WFGD instead of elemental mercury) ($Hg^0$). This in turn permits one to reduce the amount of mercury reemission that occurs from a WFGD as mercury ions (e.g., in the form of mercury (II) and/or mercury (IV)) can be controlled via a number of technologies that result in mercury recapture in a WFGD.

In still another embodiment, the present invention seeks to control the ORP in an ART so as to mitigate, reduce and/or control the amount, type and/or concentration of one or more oxidizers in a WFGD and/or the ART of a WFGD. Another benefit of this embodiment of the present invention is that it results in a reduction in the generation of various gaseous species from the ART of a WFGD. For example, when the ORP in an ART is above about 500 mV various gaseous forms of the halogens can be generated. Such halogen gas generation is undesirable as it can lead to corrosive compounds escaping the ART of a WFGD and causing corrosion issues in one or more downstream emissions control devices.

Given the above, in one embodiment the present invention relates to a method for controlling at least one parameter that is directly, or indirectly, linked to a combustion process (e.g., a fossil fuel-based combustion process, biomass combustion process, etc.) in order to optimize at least one downstream emissions control device (e.g., a wet flue gas desulfurization unit, an SCR, an ESP, a baghouse or other particulate collection device, etc.). In another embodiment, the present invention relates to a method for controlling at least one parameter that is directly, or indirectly, linked to a combustion process (e.g., a fossil fuel-based combustion process, biomass combustion process, etc.) in order to optimize at the oxidation-reduction potential in at least one downstream wet flue gas desulfurization unit.

In another embodiment the present invention relates to a method for controlling at least one parameter that is directly, or indirectly, linked to one or more emissions control device, or technology, in order to optimize at least one other upstream and/or downstream emissions control device (e.g., a wet flue gas desulfurization unit, an SCR, an ESP, a baghouse or other particulate collection device, etc.). In another embodiment, the present invention relates to a method for controlling at least one parameter that is directly, or indirectly, linked to one or more emissions control device, or technology, in order to optimize at least the oxidation-reduction potential in at least one wet flue gas desulfurization unit.

In still yet another embodiment, the present invention relates to a method for controlling at least one parameter that is directly, or indirectly, linked to a combustion process (e.g., a fossil fuel-based combustion process, biomass combustion process, etc.) in combination with controlling at least one parameter that is directly, or indirectly, linked to one or more emissions control device, or technology in order to optimize at least one other upstream and/or downstream emissions control device (e.g., a wet flue gas desulfurization unit, an SCR, an ESP, a baghouse or other particulate collection device, etc.). In still yet another embodiment, the present invention relates to a method for controlling at least one parameter that is directly, or indirectly, linked to a combustion process (e.g., a fossil fuel-based combustion process, biomass combustion process, etc.) in combination with controlling at least one parameter that is directly, or indirectly, linked to one or more emissions control device, or technology in order to optimize at least the oxidation-reduction potential in at least one wet flue gas desulfurization unit.

While specific embodiments of the present invention have been shown and described in detail to illustrate the application and principles of the invention, it will be understood that it is not intended that the present invention be limited thereto and that the invention may be embodied otherwise without departing from such principles. In some embodiments of the invention, certain features of the invention may sometimes be used to advantage without a corresponding use of the other features. Accordingly, all such changes and embodiments properly fall within the scope of the following claims.

What is claimed is:

1. A method for optimizing a wet flue gas desulfurization unit, the method comprising the steps of:
   (I) measuring, analyzing and/or controlling at least one parameter selected from the chemistry in the flue gas and/or absorber tank of the WFGD;
   (II) generating data from the at least one parameter of Step (I); and
   (III) using the data generated in Step (II) to adjust at least one operational parameter selected from at least one reagent feed flow to the wet flue gas desulfurization unit,
   wherein Step (III) comprises a method for controlling the oxidation-reduction potential in a recirculation tank, or an absorber recirculation tank, of a wet flue gas desulfurization unit, the method comprising the steps of:
   (A) supplying an aqueous solution of at least one reducing agent to a slurry, or a solution, portion of the recirculation tank, or the absorber recirculation tank, or at least one recirculation pump so that the at least one reducing agent is supplied to the wet flue gas desulfurization unit recirculation tank or absorber recirculation tank; and
   (B) permitting the at least one reducing agent to react with one or more oxidizing compounds and/or ions present in the slurry, or the solution, portion of the recirculation tank, or the absorber recirculation tank or the at least one recirculation pump, so as to achieve a reduction in the oxidation-reduction potential of the slurry, or the solution, in the recirculation tank, or the absorber recirculation tank, or in the at least one recirculation pump, or in a combination of the recirculation tank, or the absorber recirculation tank, and the at least one recirculation pump so that an amount of at least one insoluble precipitate compound in the recirculation tank, or the absorber recirculation tank, is controlled, prevented, or eliminated by the addition of the at least one reducing agent,
   wherein the at least one reducing agent is selected from phosphorous acid ($H_3PO_3$), iron (II) ammonium sulfate (($NH_4$)$_2$Fe($SO_4$)$_2$), hydroxylamine hydrochloride ($HONH_2 \cdot HCl$), hypophosphorous acid ($H_3PO_2$), or a combination of any two or more thereof.

2. A method for optimizing a wet flue gas desulfurization unit, the method comprising the steps of:
   (i) measuring, analyzing and/or controlling at least one parameter in real time selected from the chemistry in the flue gas and/or absorber tank of the WFGD;
   (ii) generating real-time data from the at least one parameter of Step (i); and
   (iii) using the real-time data generated in Step (ii) to adjust at least one operational parameter selected from at least one reagent feed flow to the wet flue gas desulfurization unit,
   wherein Step (iii) comprises a method for controlling the oxidation-reduction potential in a recirculation tank, or an absorber recirculation tank, of a wet flue gas desulfurization unit, the method comprising the steps of:
   (a) supplying an aqueous solution of at least one reducing agent to a slurry, or a solution, portion of the recirculation tank, or the absorber recirculation tank, or at least one recirculation pump so that the at least one reducing agent is supplied to the wet flue gas desulfurization unit recirculation tank or absorber recirculation tank; and
   (b) permitting the at least one reducing agent to react with one or more oxidizing compounds and/or ions present in the slurry, or the solution, portion of the recirculation tank, or the absorber recirculation tank or the at least one recirculation pump, so as to achieve a reduction in the oxidation-reduction potential of the slurry, or the solution, in the recirculation tank, or the absorber recirculation tank, or in the at least one recirculation pump, or in a combination of the recirculation tank, or the absorber recirculation tank, and the at least one recirculation pump so that an amount of at least one insoluble precipitate compound in the recirculation tank, or the absorber recirculation tank, is controlled, prevented, or eliminated by the addition of the at least one reducing agent,
   wherein the at least one reducing agent is selected from phosphorous acid ($H_3PO_3$), iron (II) ammonium sulfate (($NH_4$)$_2$Fe($SO_4$)$_2$), hydroxylamine hydrochloride ($HONH_2 \cdot HCl$), hypophosphorous acid ($H_3PO_2$), or a combination of any two or more thereof.

3. A method for optimizing a wet flue gas desulfurization unit, the method comprising the steps of:
   controlling, measuring and/or analyzing at least one process parameter of a combustion process and/or at least one combustion process air quality control system in order to yield at least one data set; and
   using the at least one data set to effect a desirable change in at least one downstream process parameter associated with one or more of a wet flue gas desulfurization unit, a particulate collection device and/or a nitrogen oxide control device, wherein the desirable change effected is accomplished by at least the measurement of an oxidation-reduction potential and using the at least one data set generated thereby to control the oxidation-reduction potential in a recirculation tank, or an absorber recirculation tank, of a wet flue gas desulfurization unit, the control method comprising the steps of:

supplying an aqueous solution of at least one reducing agent to a slurry, or a solution, portion of the recirculation tank, or the absorber recirculation tank, or at least one recirculation pump so that the at least one reducing agent is supplied to the wet flue gas desulfurization unit recirculation tank or absorber recirculation tank; and permitting the at least one reducing agent to react with one or more oxidizing compounds and/or ions present in the slurry, or the solution, portion of the recirculation tank, or the absorber recirculation tank or the at least one recirculation pump, so as to achieve a reduction in the oxidation-reduction potential of the slurry, or the solution, in the recirculation tank, or the absorber recirculation tank, or in the at least one recirculation pump, or in a combination of the recirculation tank, or the absorber recirculation tank, and the at least one recirculation pump so that an amount of at least one insoluble precipitate compound in the recirculation tank, or the absorber recirculation tank, is controlled, prevented, or eliminated by the addition of the at least one reducing agent, wherein the at least one reducing agent is selected from phosphorous acid ($H_3PO_3$), iron (II) ammonium sulfate (($NH_4$)$_2$Fe($SO_4$)$_2$), hydroxylamine hydrochloride ($HONH_2 \cdot HCl$), hypophosphorous acid ($H_3PO_2$), or a combination of any two or more thereof.

4. A method for optimizing a wet flue gas desulfurization unit, the method comprising the steps of:

controlling, measuring and/or analyzing at least two process parameters of a combustion process and/or at least one combustion process air quality control system in order to yield at least two data sets;

using the at least two data sets to effect a desirable change in at least one downstream process parameter associated with one or more of a wet flue gas desulfurization unit, a particulate collection device and/or a nitrogen oxide control device, wherein the desirable change effected is accomplished by at least the measurement of an oxidation-reduction potential and at least the concentration of at least one concentration of one or more oxidizer compounds and/or species using the at least two data sets generated thereby to control the oxidation-reduction potential in a recirculation tank, or an absorber recirculation tank, of a wet flue gas desulfurization unit, the control method comprising the steps of:

supplying an aqueous solution of at least one reducing agent to a slurry, or a solution, portion of the recirculation tank, or the absorber recirculation tank, or at least one recirculation pump so that the at least one reducing agent is supplied to the wet flue gas desulfurization unit recirculation tank or absorber recirculation tank; and permitting the at least one reducing agent to react with one or more oxidizing compounds and/or ions present in the slurry, or the solution, portion of the recirculation tank, or the absorber recirculation tank or the at least one recirculation pump, so as to achieve a reduction in the oxidation-reduction potential of the slurry, or the solution, in the recirculation tank, or the absorber recirculation tank, or in the at least one recirculation pump, or in a combination of the recirculation tank, or the absorber recirculation tank, and the at least one recirculation pump so that an amount of at least one insoluble precipitate compound in the recirculation tank, or the absorber recirculation tank, is controlled, prevented, or eliminated by the addition of the at least one reducing agent, wherein the at least one reducing agent is selected from phosphorous acid ($H_3PO_3$), iron (II) ammonium sulfate (($NH_4$)$_2$Fe($SO_4$)$_2$), hydroxylamine hydrochloride ($HONH_2 \cdot HCl$), hypophosphorous acid ($H_3PO_2$), or a combination of any two or more thereof.

5. A method for optimizing a wet flue gas desulfurization unit, the method comprising the steps of:

measuring, analyzing and/or controlling at least one parameter selected from desulfurization tower load;

generating data from the at least one parameter of the previous Step; and using the data generated in the previous Step to adjust at least one operational parameter selected from the concentration, type and/or speciation of one or more compounds and/or ions in an absorber recirculation tank solution of a desulfurization tower, wherein the method to adjust at least one operational parameter comprises at least the steps of:

supplying an aqueous solution of at least one reducing agent to a slurry, or a solution, portion of the recirculation tank, or the absorber recirculation tank, or at least one recirculation pump so that the at least one reducing agent is supplied to the wet flue gas desulfurization unit recirculation tank or absorber recirculation tank; and permitting the at least one reducing agent to react with one or more oxidizing compounds and/or ions present in the slurry, or the solution, portion of the recirculation tank, or the absorber recirculation tank or the at least one recirculation pump, so as to achieve a reduction in the oxidation-reduction potential of the slurry, or the solution, in the recirculation tank, or the absorber recirculation tank, or in the at least one recirculation pump, or in a combination of the recirculation tank, or the absorber recirculation tank, and the at least one recirculation pump so that an amount of at least one insoluble precipitate compound in the recirculation tank, or the absorber recirculation tank, is controlled, prevented, or eliminated by the addition of the at least one reducing agent, wherein the at least one reducing agent is selected from phosphorous acid ($H_3PO_3$), iron (II) ammonium sulfate (($NH_4$)$_2$Fe($SO_4$)$_2$), hydroxylamine hydrochloride ($HONH_2 \cdot HCl$), hypophosphorous acid ($H_3PO_2$), or a combination of any two or more thereof.

6. The method of claim 5, wherein the method includes a step of adding at least one of $SO_3$ or trona to an electrostatic precipitator and controlling the amount of such one or more compounds to the electrostatic precipitator so as to reduce the amount of sparking that occurs in an electrostatic precipitator while injecting one or more of $SO_3$ or trona versus the amount of sparking that occurs without such injection.

7. The method of claim 5, wherein the method includes a step of controlling the amount of sparking that occurs in an electrostatic precipitator so as to reduce the concentration and/or type of one or more oxidizers that are formed as a result of the sparking.

8. The method of claim 5, wherein the method includes a step of controlling the amount of sparking that occurs in an electrostatic precipitator so as to reduce the concentration and/or type of one or more oxidizers that are formed in the electrostatic precipitator.

9. The method of claim 8, wherein the concentration, type and/or speciation of one or more compounds and/or ions that are controlled in the absorber recirculation tank solution of the desulfurization tower include one or more oxidizers are selected from persulfate, permanganate, manganate, ozone, hypochlorite, chlorate, nitric acid, iodine, bromine, chlorine, fluorine, or combinations of any two or more thereof.

10. The method of claim 5, wherein the method permits control of both an oxidation-reduction potential and a pH in the solution of the absorber recirculation tank.

11. The method of claim 10, wherein the oxidation-reduction potential in the solution of the absorber recirculation tank is less than about 500 mV and the pH is less than about 7.

12. The method of claim 10, wherein the oxidation-reduction potential in the solution of the absorber recirculation tank is less than about 450 mV and the pH is less than about 6.5.

13. The method of claim 10, wherein the oxidation-reduction potential in the solution of the absorber recirculation tank is less than about 400 mV and the pH is less than about 6.

14. The method of claim 10, wherein the oxidation-reduction potential in the solution of the absorber recirculation tank is less than about 350 mV and the pH is less than about 6.

15. The method of claim 10, wherein the oxidation-reduction potential in the solution of the absorber recirculation tank is less than about 300 mV and the pH is less than about 6.

16. The method of claim 5, wherein the method permits control of an oxidation-reduction potential in the solution of the absorber recirculation tank so that the oxidation-reduction potential is less than about 500 mV.

17. The method of claim 5, wherein the method permits control of an oxidation-reduction potential in the solution of the absorber recirculation tank so that the oxidation-reduction potential is less than about 450 mV.

18. The method of claim 5, wherein the method permits control of an oxidation-reduction potential in the solution of the absorber recirculation tank so that the oxidation-reduction potential is less than about 400 mV.

19. The method of claim 5, wherein the method permits control of an oxidation-reduction potential in the solution of the absorber recirculation tank so that the oxidation-reduction potential is less than about 350 mV.

20. The method of claim 5, wherein the method permits control of an oxidation-reduction potential in the solution of the absorber recirculation tank so that the oxidation-reduction potential is less than about 300 mV.

21. The method of claim 5, wherein the method permits control of at least selenium speciation in the absorber recirculation tank solution while simultaneously permitting control of mercury reemission from the desulfurization unit.

22. The method of claim 5, wherein the method permits control of at least selenium speciation in the absorber recirculation tank solution.

23. The method of claim 5, wherein the method permits control of one or more of selenium speciation, manganese speciation, cobalt speciation, mercury speciation, or any two or more thereof in the absorber recirculation tank solution.

* * * * *